United States Patent [19]

Sapiejewski et al.

[11] Patent Number: 4,989,271
[45] Date of Patent: Feb. 5, 1991

[54] HEADPHONE CUSHIONING

[75] Inventors: Roman Sapiejewski, Boston; John J. Breen, Southboro, both of Mass.

[73] Assignee: Bose Corporation, Framingham, Mass.

[21] Appl. No.: 398,132

[22] Filed: Aug. 24, 1989

[51] Int. Cl.⁵ .................. A42B 1/06; H04R 5/33
[52] U.S. Cl. ............................. 2/209; 381/183
[58] Field of Search ............ 2/208, 209; 381/72, 381/74, 68.7, 183, 187

[56] References Cited

U.S. PATENT DOCUMENTS 3,073,410  1/1963  Gongoll et al. .............. 2/209
4,572,323  2/1986  Randall ...................... 181/129
4,674,134  6/1987  Lundin ....................... 2/209
4,856,118  8/1989  Sapiejewski .................. 2/209

*Primary Examiner*—Werner H. Schroeder
*Assistant Examiner*—Michael A. Neas
*Attorney, Agent, or Firm*—Fish & Richardson

[57] ABSTRACT

An improved cushion for use on a heater has a thin front skin formed with a circumferential groove. A thin flexible ring is attached to the circumferential groove. A flexible rear skin supports a foam ring and is sealed to the front skin so as to form a gel space. Structure, such as a retaining ring and mating holes and pins, attaches the cushion to the headset.

5 Claims, 1 Drawing Sheet

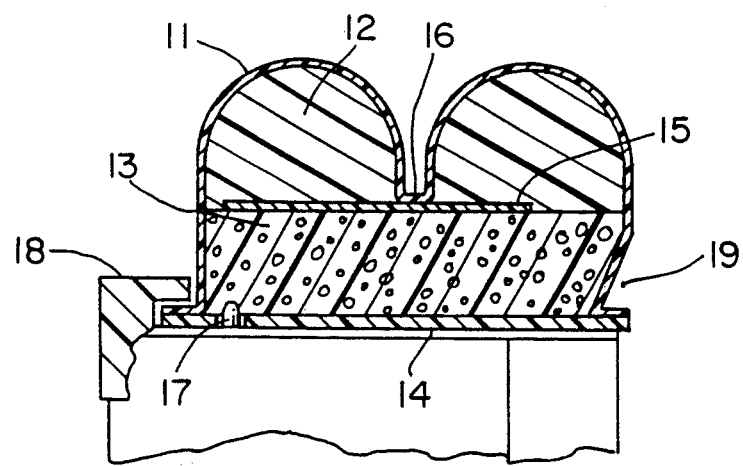

HEADPHONE CUSHIONING

BACKGROUND OF THE INVENTION

This invention relates to a set of improvements a circumaural cushion for headsets.

One prior art grooved headset cushion was formed with a groove that would disappear over time. Another problem was discomfort caused by contact between the ear and the seal on the inner edge of the cushion. Still further, the cushion was permanently difficult to replace in the case of failure.

SUMMARY OF THE INVENTION

According to the invention, an improved cushion for use on a headset comprises a thin, flexible front skin having a groove around its circumference; a thin, flexible ring which is attached to the groove in the front skin; a flexible rear skin; a foam ring which sits on the rear skin and gel. The front and rear skins are sealed such that the thin, flexible ring and the foam ring are between the skins, leaving space between the skins filled with gel. The cushion is then attached to the headset.

The thin flexible ring which is attached to the groove in the front skin preferably has a radial width about one-half that of the gel space to allow contact between the gel and foam ring and anchor the groove.

In a preferred embodiment, the inner edge of the cushion is slightly undercut to increase the clearance between the ear and the seal between the front and rear skins, thus increasing comfort. The preferred width of the undercut is approximately the width of the seal between the front and rear skins.

The cushion may attach to the headset with a number of pins on the surface of the headset engaging a number of holes in the rear skin of the cushion. The diameter of the holes is slightly larger than the diameter of the pins. A retaining ring snaps over the edge of the headset and holds the cushion against the headset.

Other features and advantages will become apparent from the following detailed description read in connection with the accompanying drawing, the single figure of which is a cross sectional view of a cushion according to the invention.

BRIEF DESCRIPTION OF THE DRAWING DETAILED DESCRIPTION

With reference to the drawing, there is shown a cross section of the cushion according to the invention having a thin front skin 11 to give the cushion its shape and retain the gel 12, a ring 13 made from a slow recovery foam and a flexible rear skin 14. A thin flexible inner ring 15 is sealed to groove 16 in the front skin 11 and trapped between gel 12 and foam ring 13.

Having described the structure of the invention, it is appropriate to consider some principles and manufacturing methods.

During the manufacturing process, front skin 11 may be first vacuum formed and then filled with gel 12. After curing the gel at an elevated temperature per the manufacturer's recommendation, typically 95 degrees C. for 120 minutes, inner ring 15 may be sealed to front skin 11 around the path formed by groove 16 which separates the two pockets of gel 12.

One of the properties of gel 12 is that it is slightly tacky, but not a good adhesive, and therefore needs sufficient surface area to provide any retention force. A likely failure mode for the cushion is when the gel portion 12 is pushed sideways (parallel to the plane of the inner ring), which generally occurs when the cushion is also in compression perpendicular to this plane. This, in the absence of ring 15 and because of the flexibility of the front skin 11, can cause the gel to fall and be trapped between the side of skin 11 and foam 13. Adhesion of the gel to the foam ring then prevents the cushion from recovering its shape when compression is removed. When deformed in this fashion, the portion of skin 11 forming groove 16 is pulled out, inverting the groove, with nothing to restore its shape after compression is removed. Addition of ring 15 minimizes these effects. Inner ring 15 preferably has enough area pinched between gel 12 and foam ring 13 and enough adhesion to gel 12 to hold inner ring 15 in place when subjected to this sideways force and thus act as an anchor for groove 16. Preferably inner ring 15 is wide enough to obtain sufficient surface contact with gel 12 to keep it from moving, and may be the same width as foam ring 13.

Even though inner ring 15 is very flexible, its edge is stiffer than the other components in the cushion and may cause some discomfort if placed in contact with the ear for a long time. In addition, some penetration of gel 12 into foam ring 13 is desirable for a good acoustic seal. Therefore, some gap is preferred between the inner edge of inner ring 15 and the vertical wall of the front skin 11. As a balance between these factors in a preferred form of cushion, this gap is approximately one-half the width of the gel width. The result is a cushion which maintains all of the acoustic and comfort properties of the cushion disclosed in U.S. application Ser. No. 07/013,339, filed Feb. 11, 1987, now U.S. Pat. No. 4,856,118, incorporated herein by reference, while increasing its long term appearance and durability.

To increase passive attenuation of ambient noise through a headphone or hearing protector, the inner edge of the cushion contacts the head over as small a circumference (fit as close around the ear) as practical. This fit is preferred for two reasons. First, the surface of the head more approximates a flat surface close to the ear so that a better seal is achieved if contact is made close to the ear (since it is easier to seal to a flat surface than an irregular one). Second, reducing cushion inner circumference reduces the area of the opening in the cushion and the noise in the earcup resulting from ambient-noise induced-vibration of the earcup relative to the head. These features are in prior art cushions.

According to the present invention, the cushion inner circumference is such that the rear edge fits under the pinna of the ear. To maintain comfort, it is preferred that the ear avoid contact with the rough edge created by the seal between the front and rear skins. This contact avoidance may be accomplished by forming the cushion with a slight undercut 19 at least the width of the seal. While more undercut may be desirable to better insure clearance to the ear, this choice provides adequate support of gel 12 over undercut 19 and allows for removing the cushion from its mold. Therefore, the width of the seal is as small as practical and undercut 19 is slightly larger than this width. The resulting cushion is very satisfactory.

The improved attachment means includes a series of pins 17 which pass through small holes in the rear skin 14 of the cushion which is in turn trapped by retaining ring 18. Pin 17 is preferably large enough to have sufficient strength to hold the cushion without breaking while the hole in the cushion is preferably small enough to prevent forming a significant acoustic leak path. The height of pin 17 is preferably tall enough to hold the cushion but short enough to avoid lifting foam ring 13 away from the earcup surface which would cause an acoustic leak. The number of pins 17 around the perimeter cf the cushion is preferably high enough to retain the entire cushion yet few enough to permit ease of alignment. The cushion retention strength is related to the height of pins 17, the amount of overlap between retaining ring 18 and the cushion lip, the thickness of rear skin 14, the distance between retaining ring 18 and pins 17, and the amount of clearance or interference between the cushion lip and retaining ring 18.

It is possible to positively retain the cushion by overlapping pin 17 with retaining ring 18 so that rear skin 14 could not fit between them. However, a breakaway design that retained the cushion adequately for most circumstances, but allowed the cushion to become disengaged rather than be damaged in an extreme situation is preferable. Thus, a preferred embodiment has eight pins 17 placed at approximately egual intervals around the perimeter of the cushion each having a diameter of 0.125 inch and the height of the cylindrical portion approximately equal to the thickness of rear skin 14. The tops of the pins are slightly tapered to make it easier to locate the cushion on them during assembly. The tapered portion is extra height above the cylindrical portion. The holes in the cushion are approximately 0.020 inch larger in diameter than the pin diameter to allow for tolerances. The distance between the edge of a pin 17 and retaining ring 18 is slightly larger than the outer lip thickness of the cushion to allow the cushion to disengage if necessary. Any of these parameters may be changed for a particular application.

To remove a cushion, the user can either make use of the breakaway design and pull up on the cushion, or retaining ring 18 may be unsnapped from the cup. To replace a cushion, the user locates the replacement cushion over pins 17 and then snaps retaining ring 18 in place to retain it.

Other embodiments are within the claims.

What is claimed is:

1. An improved cushion having an inner edge and an outer edge for use on a headset with earcups comprising:
   a thin flexible front skin having a circumferential groove,
   a thin flexible ring of a first width attached to said circumferential groove,
   a flexible rear skin,
   a foam ring which rests on said rear skin,
   said front skin sealed to said rear skin so as to form a sealed region of a fifth width having a gel space with said flexible ring and said foam ring between said front and rear skins to define inner and outer gel rings of a second and a third widths respectively,
   gel in said gel space, and
   structure for attaching said cushion to a headset.

2. The improved cushion set forth in claim 1 wherein the first width of said thin flexible ring spans substantially one-half the second width of the inner gel ring and almost substantially the full third width of the outer gel ring.

3. The improved cushion set forth in claim 1 wherein the seal between the front and rear skin at the inner edge of the cushion is formed with an under cut of a fourth width.

4. The improved cushion set forth in claim 3 wherein the fourth width of said undercut is substantially equal to the fifth width of the sealed region between said front and rear skins.

5. The improved cushion set forth in claim 1 wherein said structure for attaching comprises,
   a plurality of holes formed in said rear skin,
   a plurality of pins on the surface of said earcups which pass through said holes, and
   a retaining ring which snaps over the outer edge of the cushion.

* * * * *

UNITED STATES PATENT AND TRADEMARK OFFICE
CERTIFICATE OF CORRECTION

PATENT NO.   : 4,989,271
DATED        : February 5, 1991
INVENTOR(S)  : Roman Sapiejewski et al.

It is certified that error appears in the above-identified patent and that said Letters Patent is hereby corrected as shown below:

Column 2, line 58, "adeguate" should read --adequate--.

Column 3, line 6, "cf" should read --of--.

Column 3, line 17, "adeguately" should read --adequately--.

Column 3, line 21, "egual" should read --equal--.

Column 4, line 30, "egual" should read --equal--.

Signed and Sealed this

Fifteenth Day of December, 1992

*Attest:*

DOUGLAS B. COMER

*Attesting Officer*   *Acting Commissioner of Patents and Trademarks*